US012667574B2

(12) United States Patent
Wells et al.

(10) Patent No.: US 12,667,574 B2
(45) Date of Patent: *Jun. 30, 2026

(54) PARAXANTHINE-BASED BIOACTIVE COMPOSITION AND METHOD OF USE THEREOF

(71) Applicant: PX ING, LLC, Lewisville, TX (US)

(72) Inventors: Shawn Wells, Frisco, TX (US); Ralf Jager, Milwaukee, WI (US); Kylin Liao, Plano, TX (US); Martin Purpura, Spring, TX (US)

(73) Assignee: PX ING, LLC, Lewisville, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/965,754

(22) Filed: Oct. 13, 2022

(65) Prior Publication Data

US 2023/0115966 A1 Apr. 13, 2023

Related U.S. Application Data

(60) Provisional application No. 63/255,327, filed on Oct. 13, 2021, provisional application No. 63/255,309, filed on Oct. 13, 2021.

(51) Int. Cl.
| | |
|---|---|
| *A61K 31/522* | (2006.01) |
| *A23L 33/10* | (2016.01) |
| *A61K 31/685* | (2006.01) |
| *A61K 45/06* | (2006.01) |
| *A61P 25/28* | (2006.01) |

(52) U.S. Cl.
CPC ............ *A61K 31/522* (2013.01); *A23L 33/10* (2016.08); *A61K 31/685* (2013.01); *A61K 45/06* (2013.01); *A61P 25/28* (2018.01)

(58) Field of Classification Search
None
See application file for complete search history.

(56) References Cited

U.S. PATENT DOCUMENTS

| | | |
|---|---|---|
| 2008/0220129 A1 | 9/2008 | Cossette et al. |
| 2009/0110674 A1 | 4/2009 | Loizou |
| 2009/0325984 A1 | 12/2009 | Cosentin et al. |
| 2014/0080847 A1 | 3/2014 | Geissler |
| 2016/0038552 A1 | 2/2016 | Bredesen et al. |
| 2016/0143920 A1 | 5/2016 | Notelovitz |
| 2016/0339078 A1 | 11/2016 | Hamill |
| 2018/0105498 A1 | 4/2018 | Zemel et al. |
| 2018/0236016 A1 | 8/2018 | Gamay |
| 2019/0038640 A1* | 2/2019 | Notelovitz ........... A61K 31/593 |
| 2020/0077689 A1* | 3/2020 | Lee ....................... A23L 33/105 |
| 2021/0068429 A1 | 3/2021 | Sippy |
| 2021/0121469 A1 | 4/2021 | Bhargava |
| 2021/0169891 A1 | 6/2021 | Lelah |
| 2022/0331327 A1 | 10/2022 | Jager et al. |
| 2022/0331328 A1 | 10/2022 | Jager et al. |
| 2023/0072854 A1 | 3/2023 | Purpura et al. |

FOREIGN PATENT DOCUMENTS

| | | |
|---|---|---|
| CN | 112979651 A | 6/2021 |
| WO | 2006024545 A1 | 3/2006 |
| WO | 2010076112 A2 | 7/2010 |
| WO | 2012072670 A2 | 6/2012 |
| WO | 2012073025 A1 | 6/2012 |
| WO | 2013173265 A1 | 11/2013 |
| WO | 2014078459 A1 | 5/2014 |
| WO | WO2014065446 A1 | 5/2014 |
| WO | 2014172568 A2 | 10/2014 |
| WO | 2015131152 A1 | 9/2015 |
| WO | 2020252302 A1 | 12/2020 |
| WO | 2021151094 A1 | 7/2021 |
| WO | 2022204598 A1 | 9/2022 |

OTHER PUBLICATIONS

Damann et al., "Effects of consumption of sucromalt, a slowly digestible carbohydrate, on mental and physical energy questionnaire responses", 2013, Nutritional Neuroscience, 16, pp. 83-95 (Year: 2013).*
Decker, "Esports enthusiasts target dietary supplements to up their game", 2020, Nutritional Outlook, 23, pp. 66-70 (Year: 2020).*
Guerreiro et al., "Paraxanthine, the Primary Metabolite of Caffeine, Provides Protection against Dopaminergic Cell Death via Stimulation of Ryanodine Receptor Channels", 2008, Molecular Pharmacology, 74, Abstract Only (Year: 2008).*
Hoffman et al., "The effects of acute and prolonged CRAM supplementation on reaction time and subjective measures of focus and alertness in healthy college students", 2010, Journal of the International Society of Sports Nutrition, 7, pp. 1-8 (Year: 2010).*
Guerreiro et al., "Paraxanthine, the Primary Metabolite of Caffeine, Provides Protection against Dopaminergic Cell Death via Stimulation of Ryanodine Receptor Channels", 2008, Molecular Pharmacology, 74, pp. 980-989 (Year: 2008).*
Orrú et al., "Psychostimulant pharmacological profile of paraxanthine, the main metabolite of caffeine in humans", 2013, Neuropharmacology, 67, pp. 476-484 (Year: 2013).*
Bryan, "Psychological effects of dietary components of tea: caffeine and L-theanine", 2008, Nutrition Reviews, 66, pp. 82-90 (Year: 2008).*
Bryan, Janet , "Psychological effects of dietary components of tea: caffeine and L-theanine", Nutrition Reviews, vol. 66, 2008, 82-90.
Cornelis, Marilyn C., et al., "Genome-wide association study caffeine metabolites provides new insights to caffeine metabolism and dietary caffeine-consumption behavior", Human Molecular Genetics, vol. 25, No. 4, Oct. 3, 2016, 5472-5482.

(Continued)

*Primary Examiner* — Brenda L Coleman
*Assistant Examiner* — Madeline E Braun
(74) *Attorney, Agent, or Firm* — Dentons Davis Brown; Matthew Coryell

(57) ABSTRACT

The disclosed compositions and methods relate to compositions for human consumption comprising paraxanthine and a cholinergic agent and/or theanine. The disclosed compositions are useful for promoting cognitive function, energy, athletic performance and providing neuroprotective antioxidative effects.

16 Claims, No Drawings

(56) References Cited

OTHER PUBLICATIONS

Dammann, Kristen W., et al., "Effects of consumption of sucromalt, a slowly digestable carbohydrate, on mental and physical energy questionnaire responses", Nutritional Neuroscience, vol. 16, No. 2, 2013, 83-95.

Decker, Kimberly , "Leveling Up: Esports enthusiasts target deitary supplements to up their game", Nutritional Outlook, Apr. 1, 2020, 66-70.

Dulloo, A.G. , et al., "Paraxanthine (metabolic of caffeine) mimics caffeine's interaction with sympathetic control of thermogenesis", The American Journal of Physiology, vol. 267, No. 5, 11/1/1194, E801-E804.

Ferre, Sergi , et al., "Paraxanthine: Connecting Caffeine to Nitric Oxide Neurotransmission", Journal of Caffeine Research, vol. 3, Nov. 2, 2013.

Grgic, Jozo , et al., "CYP1A2 genotype and acute effects of caffeine on resistance of exercise, jumping, and sprinting performance", Journal of the International Society of Sports Nutrition, vol. 17, No. 21, Apr. 15, 2020, 1-11.

Guerreiro , et al., "Paraxanthine, the Primary Metabolite of Caffeine, Provides Protection Against Dopaminergic Cell Death via Stiulation of Ryanodine Receptor Channels", Molecular Pharmacology, vol. 74, 2008, 980-989.

Hoffman , et al., "The effects of acute and prolonged CRAM supplementation on reaction time and subjective measures of focus and alertness in healthy college students", Journal of the International Society of Sports Nutrition, vol. 7, 2010, 1-8.

Karami, Zohreh , et al., "Bioactive food derviced peptides: a review on correlation between structure of bioactive peptides and their functional properties", Journal of Food Science Technology, vol. 56 No. 2, Mar. 20, 2014, 535-547.

Konopelniuk, Victoria , et al., "The correction of the metabolic parameters of msg-induced obestity in rats by 2-[4-(benzyloxy) phenoxy] acetic acid", Journal of Nutrition & Intermediary Metabolism, vol. 13, Sep. 1, 2018, 1-9.

Lao-Peregrin, Cristina , et al., "Caffeine-mediated BDNF release regulates long-term synaptic plasticity through activation of IRS2 signaling", Addiction Biology, vol. 22, No. 6, Jul. 25, 2016, 1706-1718.

Monterio, Joao , et al., "Pharmacological potential of methylxanthines: Retrospective analysis and future expectations", Critical Reviews in Food and Science Nutrition, vol. 59, No. 16, May 15, 2018, 2597-2625.

Orru, Marco , et al., "Psychostimulant pharmacological profile of paraxanthine, the main metabolite of caffeine in humans", Neuropharmacology, vol. 67, 2013, 476-484.

Rothwell, Joseph A., et al., "Biomarkers of intake for coffee, tea, and sweetened beverages", Genes and Nutrition, vol. 13, No. 15, Jul. 4, 2018, 1-18.

Ryu, Sungpil , et al., "Caffeine as a Lipolytic Food Component Increase Endurance Performance in Rats and Athletes", Journal of Nutritional Science Vitaminol, vol. 47, 2001, 139-146.

Soares, Rogerio Nogueira, et al., "The influence of CYP1A2 genotype in the blood pressure response to caffeine ingestion is affected by physical status and caffeine consumption level", Vascular Pharmacology, vol. 106, Mar. 6, 2018, 67-73.

Song, Jae-Kyung , et al., "Effect of Paraxanthine on Body Fat Reduction and Insulin Sensitivity in Monosodiun Glutamate-Obsse Rats", Journal of Yeungnam Medical Science, vol. 24, No. 2, Dec. 1, 2007, 481-492.

Tartar et al. , "A Prospective Study Evaluation the Effects of a Nutritional Supplement Intervention on Cognition, Mood States, and Mental Performance in Video Gamers", Oct. 1, 2019.

Thida, Khine , "Does Caffeine Consumption before High-Intensity Intermittent Exercise Enhance Immunity?", Aukland University of Technology, 2016, 8-14, 48-54.

Vitale, Kenneth , et al., "Nutrition and Supplement Update for the Endurance Athlete: Review and Recommendations", Nutrients, Jun. 11, 2019.

Yoo et al. , "Acute Paraxanthine Ingestion Improves Cognition and Short-Term Memory and Helps Sustain Attention in a Double-Blind, Placebo-Controlled, Crossover Trial", Nov. 9, 2021.

"Are you a slow or fast metabolizer?", Green Plantation, 2023.

Carswell, Alexander T., et al., "The effect of caffeine on cognitive performance is influenced by CYP1A2 but not ADORA2A genotype, yet neither genotype affects exercise performance in healthy adults", European Journal of Applied Physiology, vol. 120, 2020, 1495-1508.

Mandal, Ananya , "Caffeine Pharmacology", News Medical, Jun. 19, 2023.

Muller, Christa , et al., "Xanthines as Adenosine Receptor Antagonists", Handb Exp Pharmacol, NIH, 2011, 1-59.

Nair, Anroop B., et al., "A simple practice guide for dose conversion between animals and humans", Journal of Basic and Clinical Pharmacy, 2016.

Schuster, Julius , et al., "More than just caffeine: psychopharmacology of methylxanthine interactions with plant-derived phytochemicals", Progress in Neuropsychopharmacology & Biological Psychiatry, vol. 89, 2019, 263-274.

St. Pierre, Brian , "All about coffee: Is it good for us?", Precise Nutrition, 2012.

* cited by examiner

PARAXANTHINE-BASED BIOACTIVE COMPOSITION AND METHOD OF USE THEREOF

CROSS-REFERENCE TO RELATED APPLICATION(S)

This application claims the benefit under 35 U.S.C. § 119 (e) to U.S. Provisional Application 63/255,309, filed Oct. 13, 2021, and entitled PARAXANTHINE-BASED BIOACTIVE COMPOSITION AND METHOD OF USE THEREOF, and U.S. Provisional Application 63/255,327, filed Oct. 13, 2021, and entitled PARAXANTHINE-BASED BIOACTIVE COMPOSITION AND METHOD OF USE THEREOF, each of which is hereby incorporated herein by reference in its entirety for all purposes.

TECHNICAL FIELD

The disclosed technology relates generally to compositions, methods, and system for utilizing paraxanthine alone and in combination for use in providing physiological benefits. More particularly, the disclosure relates to paraxanthine and other compounds, whether produced synthetically or derived from natural sources, and use of these chemical compounds to provide physiological benefits, which may vary according to paraxanthine concentration and the presence of synergists and antagonists.

BACKGROUND

Paraxanthine, also known as 1,7-dimethylxanthine or 1,7-Dimethyl-3H-purine-2,6-dione, is a dimethyl derivative of xanthine, structurally related to caffeine as well as a metabolite of caffeine. In humans and other animals caffeine is first degraded to either paraxanthine (1, 7-dimethylxanthine), theobromine or theophylline. Paraxanthine is observed in nature as a metabolite of caffeine in animals and humans. Paraxanthine is also found naturally occurring in various plant species, such as *Citrus paradisi* (grapefruit), *Theobroma cacao* (cocoa) and *Camilia sinensis* (tea).

Caffeine is a bitter, white crystalline purine, a methylxanthine alkaloid, and is chemically related to the adenine and guanine bases of deoxyribonucleic acid (DNA) and ribonucleic acid (RNA). It is found in the seeds, nuts, or leaves of a number of plants native to Africa, East Asia and South America, and helps to protect them against predator insects and to prevent germination of nearby seeds. The most well-known source of caffeine is the coffee bean, a misnomer for the seed of Coffea plants.

Caffeine is by far the most studied, and the most commonly used stimulant found in coffee and tea products. Paraxanthine appears to have an improved effect over caffeine, despite being very similar in chemical structure. Recent experiments have shown that paraxanthine exhibits a variety of activities, some of which seem inconsistent.

Concerns about potential health risks of coffee and caffeine consumption raised by epidemiological research in the past were likely exacerbated by associations between high intakes of coffee and unhealthy behaviors, such as cigarette smoking and physical inactivity. More recently, coffee consumption has been associated with reductions in the risk of several chronic diseases.

Caffeine concentrations in coffee beverages can be quite variable. A standard cup of coffee is often assumed to provide 100 mg of caffeine, but a recent analysis of 14 different specialty coffees purchased at coffee shops in the US found that the amount of caffeine in 8 oz (~240 ml) of brewed coffee ranged from 72-130 mg (McCusker, R. R., Goldberger, B. A. and Cone, E. J. 2003. Caffeine content of specialty coffees. J. Anal. Toxicol., 27:520-522.). Caffeine in espresso coffees ranged from 58-76 mg in a single shot. Interestingly, the caffeine content of the same type of coffee purchased from the same store on six separate days varied from 130 to 282 mg per 8-oz serving.

Thus, there is a need in the art to identify alternative chemical compounds and mixtures thereof that may provide benefits. It is also desirable to provide chemical compounds and mixtures thereof that may be used to provide a variety of benefits, varying by concentration, thus requiring production of fewer materials.

BRIEF SUMMARY

This disclosure relates to the use of a chemical composition comprising paraxanthine, either naturally or synthetically produced, and optionally other chemicals, including paraxanthine congeners or analogs, to provide a plurality of desirable effects. Paraxanthine analogs may include, but are not limited to, caffeine, methyl caffeine, theobromine, theacrine, theophylline, liberine and methylliberine, and their variants. Other suitable actives may include one or more ergogenic or nootropic compounds such, St John's Wort, sulbutiamine, methylcobalamin and the like.

Paraxanthine exhibits a wide variety of effects depending on dosage. The presence of other ingredients may also modulate its effects. It may be used to improve endurance performance, mood, promote calm and focus, vigor, lipolysis, energy expenditure, exercise performance, and/or decreased appetite. It may also serve as an antioxidant and an anti-inflammatory.

In one embodiment, paraxanthine may be used to modulate stimulants, to provide heightened energy without heightened anxiety or nervousness. There may be variability among individuals, as described herein.

In another embodiment paraxanthine may be used as a mild mood enhancer or relaxant.

In a further embodiment, paraxanthine may be used to promote weight loss by reducing appetite, act as an antioxidant and as an anti-inflammatory. Paraxanthine may be used transdermally to enhance one or more of these effects.

In one embodiment, a dietary supplement comprising about 2 mg to about 800 mg paraxanthine, either natural through fermentation or synthetic, is provided.

In another embodiment, a method of treatment for improving physical performance or energy in an individual is provided. This method involves providing the individual with a composition comprising about 2 mg to about 800 mg of paraxanthine, either natural or synthetic, wherein upon administration of the composition the individual experiences improvement of at least one of endurance performance, mood, promote calm and focus, vigor, lipolysis, energy expenditure, exercise performance, and/or decreased appetite. In another embodiment, a second compound such as caffeine may also be administered in the composition.

It is therefore an object of the present disclosure to provide compositions including paraxanthine capable of imparting a plurality of positive effects.

It is another object of the present disclosure to provide congeners, derivatives and iterations of paraxanthine and synthetic chemical equivalents of paraxanthine.

It is another object of the present disclosure to provide agglomerated paraxanthine, paraxanthine salts, microencapsulated, liposomal or esterified paraxanthine.

It is another object of the present disclosure to provide paraxanthine combined with glycerides, propylene glycol, polyethylene glycol (PEG), lauroyl macrogol, lauroyl macrogol derivatives and co-crystallization products of paraxanthine.

While multiple embodiments are disclosed, still other embodiments of the disclosure will become apparent to those skilled in the art from the following detailed description, which shows and describes illustrative embodiments of the disclosed compositions, systems and methods. As will be realized, the disclosed compositions, systems and methods are capable of modifications in various obvious aspects, all without departing from the spirit and scope of the disclosure. Accordingly, the detailed description is to be regarded as illustrative in nature and not restrictive.

DETAILED DESCRIPTION

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "subject" refers to the target of administration, e.g., an animal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause unacceptable adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Compositions

Disclosed are compositions comprising a combination of paraxanthine and a cholinergic agent and the related uses thereof. Further disclosed herein are compositions comprising a combination of paraxanthine and theanine and the related uses thereof. Paraxanthine may be produced synthetically or may be isolated from a natural source or through fermentation. Paraxanthine isolated from such sources may be purified to 95% or greater purity. Optionally, less purification may be used such that combination of paraxanthine for 50%, or even less, of the material. In some embodiments, it may be preferable to utilize paraxanthine isolated from a natural source which may include other congeners of paraxanthine typically found in paraxanthine sources.

In certain embodiments, the composition is formulated such that a dose contains paraxanthine ranging from about 1 to about 1000 mg (e.g., about 1 mg, about 5 mg, about 10 mg, about 15 mg, about 20 mg, about 25 mg, about 30 mg, about 35 mg, about 40 mg, about 45 mg, about 50 mg, about 75 mg, 100, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg, and the like, or any range or value therein).

In certain embodiments, the cholinergic agent is a choline source. In exemplary implementations, the choline source is choline salt (e.g., an organic or inorganic choline salt). In particular, the choline salt can be selected from the group consisting of choline chloride, choline bitartrate, choline hydroxide, choline citrate and choline carbonate. In particular, the choline salt can be choline chloride or choline bitartrate. The choline compositions can also contain a blend of one or more choline salts, such as a mixture of choline chloride and choline bitartrate.

According to certain further embodiments, the cholinergic agent functions to increase cholinergic tone, such as by increasing choline synthesis and/or increasing choline/acetylcholine release. Examples include, but are not limited to phosphatidylserine (e.g., acetyl-L-Carnitine), huperzine A (e.g., club moss extract), bacopa monnieri, ashwagandha, rhodiola, lion's mane, guarana, yerbamate, gotu kola, kola nut, sulbutiamine, methylcobalamin, L-theanine, *Ginkgo biloba, Ginseng*, tetrahydrocurcumin creatine, and/or fish oil. In certain further embodiments, the cholinergic agent is a secondarily butyrylcholinesterase inhibitor. In further aspects, the cholinergic agent is chosen from phosphatidylcholine, alpha-GPC (L-alpha glycerylphosphorylcholine), Citicoline (Cytidine diphosphate choline (CPD Choline)), Choline Bitartrate, Bacopa Monnieri, Phosphatidylserine, pilocarpine, and cevimeline, *Amburana cearensis, Lippia sidoides, Paullinia cupana, Plathymiscium floribundum* and *Solanum asperum* and/or combinations thereof. In still further aspects, the composition further comprises a pharmaceutically acceptable carrier.

In certain embodiments, the composition is formulated such that a dose contains a cholinergic agent ranging from about 1 to about 1000 mg (e.g., about 1 mg, about 5 mg, about 10 mg, about 15 mg, about 20 mg, about 25 mg, about 30 mg, about 35 mg, about 40 mg, about 45 mg, about 50 mg, about 75 mg, 100, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg, and the like, or any range or value therein).

Theanine, also known as L-γ-glutamylethylamide and N5-ethyl-L-glutamine, is an amino acid analogue of the proteinogenic amino acids L-glutamate and L-glutamine and is found primarily in particular plant and fungal species.

In certain embodiments, theanine is present in the composition in the amount of about 25 mg to about 650 mg.

In certain embodiments, the composition is formulated such that a dose contains theanine ranging from about 1 to about 1000 mg (e.g., about 1 mg, about 5 mg, about 10 mg, about 15 mg, about 20 mg, about 25 mg, about 30 mg, about 35 mg, about 40 mg, about 45 mg, about 50 mg, about 75 mg, 100, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg, and the like, or any range or value therein).

In certain embodiments, the weight to weight ratio of paraxanthine to theanine is from about 0.5:1 to about 50:1. In further embodiments, the weight to weight ratio of paraxanthine to theanine is from about 1:1 to about 10:1. In yet further embodiments, the weight to weight ratio of paraxanthine to theanine is from about 2:1 to about 4:1 of about 25 mg to about 650 mg In further embodiments, the disclosed supplement further comprises a paraxanthine congener or paraxanthine analog. In exemplary aspects of these embodiments, the paraxanthine congener or analog is selected from the group consisting of caffeine, methyl caffeine, theobromine, theophylline, liberine, methylliberine, theacrine and combinations thereof. In still further aspects, the paraxanthine congener or analog is caffeine.

In certain embodiments, the composition is substantially free of caffeine.

According to certain embodiments, the disclosed the supplement is in a solid oral dosage form. In yet further embodiments, the supplement is in a topical form.

According to still further embodiments, the disclosed composition comprising paraxanthine and a cholinergic agent and/or theanine is in the form of a drink.

Further disclosed herein is a method for improving physical performance or energy in subject, comprising providing the subject with a composition comprising about 2 mg to about 800 mg of paraxanthine and a cholinergic agent. In exemplary aspects, the subject experiences improvement of at least one of mood, energy, focus, concentration or sexual desire or a reduction of at least one of anxiety or fatigue.

In certain implementations of the disclosed method paraxanthine is present in the composition in amount from about 50 mg to about 400 mg.

In certain embodiments, the subject experiences a decrease in fatigue of at least about 6 percent, following administration of the composition. In further embodiments, the subject experiences an increase in energy of at least about 8 percent, following administration of the composition.

According to certain implementations of the disclosed method, composition provided to the subject further comprises at least one ingredient selected from the group consisting of caffeine, theobromine, naringin, hesperidin, 2-(dimethylamino) ethanol (DMAE), DMAE bitartrate, choline bitartrate, alpha-GPC, huperzine A, and CDP choline.

Further disclosed herein is a method treating a condition in a subject in need thereof, comprising administering to the subject a composition comprising paraxanthine, a cholinergic agent, and a pharmaceutically acceptable carrier thereof. In certain implementations, the condition is selected from narcolepsy, epilepsy, attention deficit disorders, attention deficit hyperactivity syndrome (ADHD), cognitive deficit disorders, palsies, uncontrolled anger, migraine, substance abuse addictions, eating disorders, depression, anxiety disorders, traumatic head injury (TBI), Parkinson's disease, Alzheimer's, and dementia.

In certain aspects of these embodiments, paraxanthine is present from about 2 mg to about 800 mg. In further aspects, the cholinergic agent is chosen from phosphatidylcholine, alpha-GPC (L-alpha glycerylphosphorylcholine), Citicoline (Cytidine diphosphate choline (CPD Choline)), Choline Bitartrate, Bacopa Monnieri, Phosphatidylserine, pilocarpine, and cevimeline.

According to certain embodiments of the disclosed method, the composition is administered in a therapeutically effective amount. In further embodiments, the composition is administered in a prophylactically effective amount.

Further disclosed herein is a method of enhancing attention in a subject in need thereof comprising administering a composition to the subject comprising paraxanthine and a cholinergic agent. Further disclosed herein is a method of improving working memory in a subject in need thereof comprising administering a composition to the subject comprising paraxanthine and a cholinergic agent. Further disclosed herein is a method of improving cognitive performance in a subject comprising administering a composition to the subject comprising paraxanthine and a cholinergic agent.

Further disclosed herein is a method of enhancing attention in a subject in need thereof comprising administering a composition to the subject comprising paraxanthine and theanine. Further disclosed herein is a method of improving working memory in a subject in need thereof comprising administering a composition to the subject comprising paraxanthine and theanine. Further disclosed herein is a method of improving cognitive performance in a subject comprising administering a composition to the subject comprising paraxanthine and a theanine.

In certain embodiments, paraxanthine-cholinergic agent composition and/or paraxanthine-theanine composition may be combined with one or more other chemical compounds (e.g. other active ingredients), to provide a plurality of positive effects in a subject. By altering the dosage of paraxanthine and/or chemical compounds it is combined with, various physiological effects may be selected for. The compositions may provide primarily a single benefit, or may provide multiple benefits simultaneously.

In certain embodiments, paraxanthine is combined with one or more additional active ingredients selected from: a group consisting of: gallic acid, (+)-catechin (C), (−)-epicatechin (EC), (+)-gallocatechin (GC), (−)-epigallocatechin (EGC), (−)-catechin gallate (CG), (−)-gallocatechin gallate (GCG), (−)-epicatechin gallate (ECG) and (−)-epigallocatechin gallate (EGCG), glycerides, propylene glycol, lauroyl macrogol, lauroyl macrogol derivatives, co-crystallization products of bioperine, piperine, black pepper, bergamottin, dihydroxybergamottin (CYP3A4), flavonoids (naringin, hesperidin, nobiletin, tangeretin, quercetin), pterostilbene, fisetin, phytosomes, salicin, fish oil (omega-3 fatty acids and specialized, small lipid pro-resolving epoxide derivatives), oxylipins, tart cherry, krill oil, astaxanthin, proteolytic enzymes, glucosamine sulfate, chondroitin (methylsulfonylmethane), SAMe (S-adenosylmethionine), ASU (avocadosoybean unsapponifiable fraction), cetyl myristoleate, *Dolichos* falcate, triterpenoids, *Acacia catechu, Andrographis paniculata, Scutalleria baicalensis, Agmatine sulfate, Stinging Nettle, Sea Buckthorn, Curcumin, Cissus Quadrilangularis, Boswellia Serrata, Wasabia japonica* (wasabi extract for Tea Tree Oil), Emu Oil, *Arnica, Mangifera indica* L. (Anacardiaceae), *Lagenaria breviflora, Zingiber officinale* (ginger & gingerols/shogaols), *Hoodia gordonii,* caffeine, yohimbine, methylsynephrine, synephrine, theobromine, flavenoids, tocopherols, theophylline, alphayohimbine, conjugated linoleic acid (CLA), octopamine, evodiamine, passion flower, red pepper, cayenne, raspberry ketone, guggul, green tea, guarana, kola nut, beta-Phenethylamines, *Acacia rigidula,* forskolin (*Coleus forskohlli*), theophylline, synephrine, yohimbine, *Rhodiola,* ashwagandha, *Ginseng, Ginkgo biloba,* siberian *Ginseng, Astragalus,* licorice, green tea, reishi, dehydroepiandrosterone (DHEA), pregnenolone, tyrosine, N-acetyl-tyrosine, glucuronolactone, taurine, Acetyl-L-carnitine, 5-hydroxytryptophan, tryptophan, Phenethylamines, *Sceletium tortuosum* (and Mesembrine alkaloids), Dendrobium sp., *Acacia*

*rigidula,* PQQ (Pyroloquinoline quinone), Ubiquinone(01), *Nicotinamide riboside,* picamilon, Huperzine A (Chinese clubmoss or *Huperzia serrata,* L-dopa, *Mucuna pruriens,* and forskolin (*Coleus forskohlli*), 2-(dimethylamino) ethanol (DMAE), DMAE bitartrate, and combinations thereof.

In another embodiment, paraxanthine may be used at lower dosage levels and/or in conjunction with compounds that modulate or antagonize its activity. Such compositions may induce an improved endurance performance, mood, vigor, lipolysis, energy expenditure, exercise performance, and/or decreased appetite.

An advantage of using the invention may be the reduced likelihood that a person develops a tolerance to chemical compositions in accordance with the principles of the invention. That is, a person may not become desensitized to the effects induced.

According to certain aspects, the disclosed paraxanthine-cholinergic agent containing compositions has at least the following distinct advantages over the administration of compositions containing comparable doses of caffeine. Paraxanthine has substantially lower toxicity. Paraxanthine containing compositions are more potent wake-promoting agent (in certain embodiments, via adenosine receptor antagonism). Further, Paraxanthine containing compositions enhance striatal dopaminergic tone. Still further, paraxanthine does not produce sleep rebound. Yet further, paraxanthine does not enhance anxiety.

In another embodiment, paraxanthine may be used at higher dosage levels and/or with synergistic compounds. These compositions may increase a person's basal/resting metabolic rate, increase thermogenesis, decrease appetite, enhance cognitive performance, increase Alpha wave brain activity, and/or induce euphoria. Without being bound by theory, the inventors believe that at higher dosage levels, paraxanthine may be noradrenergic and dopaminergic, and may exhibit increased adenosine receptor inhibition.

In another embodiment, paraxanthine-cholinergic agent composition is combined with ephedrine, caffeine, salicylic acid or the like. The foregoing combinations may produce a synergistic effect with the stimulating effects of paraxanthine. For example, in certain embodiments, paraxanthine-cholinergic agent composition is be combined with much lesser amounts of caffeine in order to modulate the excessive stimulatory effects of caffeine, thereby stabilizing heart rate and other metabolic activity. That is, a combination of paraxanthine and caffeine may result in a composition that imparts the increased focus and energy induced by caffeine, but without the higher heart rate and blood pressure due to modulation of caffeine's effects by paraxanthine. Thus the combination may result in heightened awareness and calmness without the jitters caffeine may cause.

Nutritional Supplements

The compositions of the disclosure may take the form of dietary supplements or may themselves be used in combination with dietary supplements, also referred to herein as food supplements.

Nutritional supplements may be found in many forms such as tablets, capsules, soft gels, gel caps, liquids, or powders. Some dietary supplements can help ensure an adequate dietary intake of essential nutrients; others may help reduce risk of disease.

Food Products

The compositions of the disclosure may take the form of a food product. Here, the term "food" is used in a broad sense and covers food and drink for humans as well as food and drink for animals (i.e. a feed). Preferably, the food product is suitable for, and designed for, human consumption.

The food may be in the form of a liquid, solid or suspension, depending on the use and/or the mode of application and/or the mode of administration.

When in the form of a food product, the composition may comprise or be used in conjunction with one or more of: a nutritionally acceptable carrier, a nutritionally acceptable diluent, a nutritionally acceptable excipient, a nutritionally acceptable adjuvant, a nutritionally active ingredient.

By way of example, the compositions of the disclosure may take the form of one of the following: A fruit juice; a beverage comprising whey protein: a health or herbal tea, a cocoa drink, a coffee drink, a yoghurt and/or a drinking yoghurt, a cheese, an ice cream, a desserts, a confectionery, a biscuit, a cake, cake mix or cake filling, a snack food, a fruit filling, a cake or doughnut icing, an instant bakery filling cream, a filling for cookies, a ready-to-use bakery filling, a reduced calorie filling, an adult nutritional beverage, an acidified soy/juice beverage, a nutritional or health bar, a beverage powder, an energy drink, a sublingual, a gummy, a calcium fortified soy milk, or a calcium fortified coffee beverage.

Food Ingredients

Compositions of the present disclosure may take the form of a food ingredient and/or feed ingredient.

As used herein the term "food ingredient" or "feed ingredient" includes a composition which is or can be added to functional foods or foodstuffs as a nutritional and/or health supplement for humans and animals.

The food ingredient may be in the form of a liquid, suspension or solid, depending on the use and/or the mode of application and/or the mode of administration.

Functional Foods

Compositions of the disclosure may take the form of functional foods. As used herein, the term "functional food" means food which is capable of providing not only a nutritional effect but is also capable of delivering a further beneficial effect to the consumer.

Accordingly, functional foods are ordinary foods that have components or ingredients (such as those described herein) incorporated into them that impart to the food a specific function—e.g. medical or physiological benefit—other than a purely nutritional effect.

Although there is no legal definition of a functional food, most of the parties with an interest in this area agree that they are foods marketed as having specific health effects beyond basic nutritional effects.

Some functional foods are nutraceuticals. Here, the term "nutraceutical" means a food which is capable of providing not only a nutritional effect and/or a taste satisfaction, but is also capable of delivering a therapeutic (or other beneficial) effect to the consumer. Nutraceuticals cross the traditional dividing lines between foods and medicine.

Medical Foods

Compositions of the present disclosure may take the form of medical foods. By "medical food" it is meant a food which is formulated to be consumed or administered with or without the supervision of a physician and which is intended for a specific dietary management or condition for which distinctive nutritional requirements, based on recognized scientific principles, are established by medical evaluation.

Athletic Performance

Further disclosed herein is a method for enhancing performance or energy in subject, comprising administering to the subject a composition disclosed herein. As used herein the term "enhancing performance" is intended to mean any improvement in performance. Performance can be assessed in any manner. Certain enhancements are readily measured. For example, in a timed-event, an improved time can assess an enhanced performance. Certain performance enhancing properties can be judged subjectively by the athlete or performer or an observer. In these instances, an enhanced performance means that the performance was perceived subjectively to be improved, magnified, faster, better and the like. In certain embodiments, the disclosed methods are used to enhance athletic performance. "Athletic performance" refers to any professional or recreational activity wherein the performer, for example an athlete, exerts a physical act, such as running, swimming, golf, bowling, archery, football, baseball, basketball, soccer, hiking, cycling, dancing and the like. In certain athletic performance is improved through in improvement of endurance in the subject. In other words, administration of the disclosed compositions improves a subject's level of endurance, thereby enhancing the subject's athletic performance. In further embodiments, administration of the composition to the subject increases cognitive performance which thereby improves athletic performance.

In certain embodiments, upon administration of the composition, the subject experiences improvement of at least one of mood, energy, focus, concentration or sexual desire or a reduction of at least one of anxiety, fatigue, perception of effort or perception of pain.

In further embodiments, upon continued administration to the subject, the composition does not create dependence in the subject and/or withdrawal effect in the subject when continued use is ceased.

Further disclosed herein is a method of increasing athletic endurance in a subject comprising administering to the subject a composition disclosed herein. In certain implementations, the composition administered to the subject comprises paraxanthine and tyrosine. In exemplary implementations, the administration of paraxanthine and a cholinergic agent produce a synergistic increase in athletic endurance in the subject, relative to the administration of paraxanthine or the cholinergic agent alone.

Further disclosed herein is a method of increasing athletic endurance in a subject comprising administering to the subject a composition disclosed herein. In certain implementations, the composition administered to the subject comprises paraxanthine and tyrosine. In exemplary implementations, the administration of paraxanthine and theanine produce a synergistic increase athletic endurance in the subject, relative to the administration of paraxanthine or theanine alone.

In another embodiment, paraxanthine may be used as a topical agent for incorporation into body creams or lotions to produce a cream or lotion for lightening skin, firming skin, and/or improving skin elasticity. A paraxanthine topical agent may also be used to promote localized transdermal fat loss. Paraxanthine may also be used in a cream or lotion to promote localized enhanced metabolism and/or enhanced thermogenesis.

According to further embodiments, the paraxanthine-cholinergic agent composition is be combined with one or more of analgesics and/or anti-inflammatory agents. In exemplary implementations, paraxanthine is combined with ibuprofen, salicylic acid, anti-inflammatory agents, salicin, fish oil (omega-3 fatty acids and specialized, small lipid pro-resolving derivatives), tart cherry, krill oil, astaxanthin, proteolytic enzymes, glucosamine sulfate, chondroitin sulfate, MSM (methylsulfonylmethane), SAMe (S-adenosylmethionine), ASU (avocado-soybean unsapponifiable fraction), cetyl myristoleate, *Dolichos falcate* and/or triterpenoids.

In another embodiment, the paraxanthine-cholinergic agent composition is combined with one or more bioavailability enhancers. In exemplary embodiments, bioavailability enhancers include, but are not limited to: bioperine, piperine, black pepper, bergamottin, dihydroxybergamottin (CYP3A4 inhibitors), flavonoids (including hesperidin, naringin, tangeritin, quercetin and nobiletin both in isolation and in combination), pterostilbenes, fisetin, nanoencapsulation, microencapsulation, liposomes and/or phytosomes. Which enhancers are combined with paraxanthine may depend on which qualities of paraxanthine are desired for a particular use.

In another embodiment, the paraxanthine-cholinergic agent composition may be administered using one or more delivery methods, including, for example transdermal patches and/or creams, ready to mix powders, intravenous methods, capsules, tablets, liquid (including liquids for mixing with other beverages), softgels, shot format, and/or cosmetic applications including soaps, lotions and shampoos. Paraxanthine's anti-inflammatory qualities may be desired for a variety of topical applications.

Cognitive Function

Disclosed herein is a method of enhancing cognitive function in a subject comprising administering to the subject a composition disclosed herein. In certain embodiments, improved cognitive function is measured by an increase in one or more of: attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behavior, speed of processing, reasoning, problem solving and/or social cognition.

In certain embodiments, administration of the disclosed composition increases working memory.

In further embodiments, administration of the disclosed composition increases attention.

According to certain embodiments, composition of the instantly disclosed methods to enhance cognitive function further comprise tyrosine, N-acetyl-tyrosine, taurine, huperzine A, acetyl-l-carnitine, CDP choline, Alpha GPC, choline bitrate, choline citrate, B12, caffeine, methyllliberine, theacrine, paraxanthine, theobromine, ashwagandha, *Rhodiola*, lutein, zeaxanthin, fish oil, creatine, *Ginseng*, lions mane, niacin, *Cordyceps*, theanine, B-vitamins, GABA, sulbutiamine, vinpocetine, adenosine triphosphate, inositol, enhanced arginine silicate, nitrates, electrolytes, hesperidin and derivatives of hesperidin and/or bacopa.

In certain embodiments, the subject has experience age-related cognitive decline. In exemplary implementations, administration of the composition to the subject increases the level BDNF in the subject. According to certain embodiments, administration of the composition to the subject increases brain derived neurotrophic factor (BDNF) levels in the subject. In exemplary implementations, BDNF levels are increased by from about 5% to about 40%. In further embodiments, BDNF levels are increased by at least about 15%. In further embodiments, administration of the composition to the subject increases other neurotrophic factors such as neuronal growth factor (NGF).

Methods of Treatment

According to certain embodiments, the composition disclosed herein are used in the treatment of one or more medical conditions in a subject in need thereof. In certain implementations, the disclosed composition is administered to a subject suffering from narcolepsy, sleep apnea, and shift work sleep disorder, insomnia epilepsy, attention deficit disorders, attention deficit hyperactivity syndrome (ADHD), cognitive deficit disorders, palsies, uncontrolled anger, migraine, substance abuse addictions, eating disorders, depression, anxiety disorders, traumatic head injury (TBI), Parkinson's disease, Alzheimer's, and/or dementia.

In certain aspects, the disclosed compositions are a neuroprotective agent. In certain embodiments, administration of the disclosed compositions to a subject in need thereof is neuroprotective. In exemplary aspects of these embodiments, this neuroprotection is in the form of protecting against dopaminergic cell death.

Further disclosed herein is a method for treating or preventing age-related cognitive decline in a subject in need thereof, comprising administering to the subject an effective amount of a composition disclosed herein. In certain embodiments, administration of the composition increases one or more of attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behavior, speed of processing, reasoning, problem solving and/or social cognition. In certain implementations, administration of the composition to the subject increases levels of catalase and/or glutathione in the subject. In further implementations, the composition administered to the subject comprises paraxanthine and cholinergic agent and the administration of paraxanthine and cholinergic agent produce a synergistic increase in catalase and/or glutathione in the subject, relative to the administration of paraxanthine or cholinergic agent alone.

According to still further embodiments, administration of the composition to the subject increases BDNF in the subject. In further implementations, the composition administered to the subject comprises paraxanthine and cholinergic agent and the administration of paraxanthine and cholinergic agent produce a synergistic increase in BDNF in the subject, relative to the administration of paraxanthine or cholinergic agent alone.

The administration of the disclosed compositions to a subject may include any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, intradermal administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

Various aspects and embodiments of the present invention are defined by the following numbered clauses:

Various aspects and embodiments of the present invention are defined by the following numbered clauses:

1. A composition comprising a first active ingredient comprising about from 2 mg to about 800 mg paraxanthine and a cholinergic agent.

2. The composition of clause 1, wherein paraxanthine is present in amount from about 20 mg to about 600 mg.

3. The composition of clause 2, wherein paraxanthine is present in amount from 50 mg to about 400 mg.

4. The composition of clauses 1-3, wherein the cholinergic agent is selected from: phosphatidylcholine, alpha-GPC (L-alpha glycerylphosphorylcholine), Citicoline (Cytidine diphosphate choline (CPD Choline)), Choline Bitartrate, Bacopa Monnieri, Phosphatidylserine, pilocarpine, and cevimeline *Amburana cearensis, Lippia sidoides, Paullinia cupana, Plathymiscium floribundum*, tetrahydrocurcumin, and *Solanum asperum* and/or combinations thereof.

5. A composition comprising paraxanthine and theanine.

6. The composition of clause 5, wherein the paraxanthine and theanine are each present in an amount from about 2 mg to about 800 mg.

7. The composition of clause 6, wherein the paraxanthine and the theanine agent are each present in an amount from about 20 mg to about 600 mg.

8. The composition of clause 7, wherein the paraxanthine and theanine are each present in an amount from about amount from 50 mg to about 400 mg.

9. The composition of any of clauses 5-8, further comprising one or more of an active selected from a group consisting of: L-theanine, phosphatidylcholine, alpha-GPC (L-alpha glycerylphosphorylcholine), Citicoline (Cytidine diphosphate choline (CPD Choline)), Choline Bitartrate, Bacopa Monnieri, Phosphatidylserine, pilocarpine, and cevimeline *Amburana cearensis, Lippia sidoides, Paullinia cupana, Plathymiscium floribundum*, tetrahydrocurcumin, and *Solanum asperum* and/or combinations thereof, gallic acid, (+)-catechin (C), (−)-epicatechin (EC), (+)-gallocatechin (GC), (−)-epigallocatechin (EGC), (−)-catechin gallate (CG), (−)-gallocatechin gallate (GCG), (−)-epicatechin gallate (ECG) and (−)-epigallocatechin gallate (EGCG), glycerides, propylene glycol, lauroyl macrogol, lauroyl macrogol derivatives, co-crystallization products of bioperine, piperine, black pepper, bergamottin, dihydroxybergamottin (CYP3A4), flavonoids (naringin, hesperidin, nobiletin, tangeretin, quercetin), pterostilbene, fisetin, phytosomes, salicin, fish oil (omega-3 fatty acids and specialized, small lipid pro-resolving epoxide derivatives), oxylipins, tart cherry, krill oil, astaxanthin, proteolytic enzymes, glucosamine sulfate, chondroitin sulfate, MSM (methylsulfonylmethane), SAMe (S-adenosylmethionine), ASU (avocado-soybean unsapponifiable fraction), cetyl myristoleate, *Dolichos falcate*, triterpenoids, *Acacia catechu, Andrographis paniculata, Scutalleria baicalensis*, Agmatine sulfate, Stinging Nettle, Sea Buckthorn, Curcumin, Cissus Quadrilangularis, *Boswellia serrata, Wasabia japonica* (wasabi extract for Tea Tree Oil), Emu Oil, *Arnica, Mangifera indica* L. (Anacardiaceae), *Lagenaria breviflora, Zingiber officinale* (ginger & gingerols/shogaols), *Hoodia gordonii*, caffeine, yohimbine, methylsynephrine, synephrine, theobromine, flavenoids, tocopherols, theophylline, alpha-yohimbine, conjugated linoleic acid (CLA), octopamine, evodiamine, passion flower, red pepper, cayenne, raspberry ketone, guggul, green tea, guarana, kola nut, beta-Phenethylamines, *Acacia rigidula*, forskolin (*Coleus forskohlli*), theophylline, synephrine, yohimbine, *Rho-

*diola*, ashwagandha, *Ginseng, Ginkgo biloba*, siberian *Ginseng, astragalus*, licorice, green tea, reishi, dehydroepiandrosterone (DHEA), pregnenolone, tyrosine, N-acetyl-tyrosine, glucuronolactone, taurine, Acetyl-L-carnitine, 5-hydroxytryptophan, tryptophan, Phenethylamines, *Sceletium tortuosum* (and Mesembrine alkaloids), Dendrobium sp., *Acacia rigidula*, PQQ (Pyroloquinoline quinone), Ubiquinone(01), *Nicotinamide riboside*, picamilon, Huperzine A (Chinese clubmoss or *Huperzia serrata*, L-dopa, *Mucuna pruriens*, and forskolin (*Coleus forskohlli*), 2-(dimethylamino) ethanol (DMAE), DMAE bitartrate, medium chain triglycerides, creatine, citrulline, arginine, lions mane, cordyceps, leucine, isoleucine, valine, BAIBA, ergothioneine, grains of paradise, Kanna, Huperzine A, ketones, Maca, *Ginseng*, ashwagandha, *Rhodiola*, theanine BCAAs, beta-alanine, fish oil, citrulline, arginine, HMB, HICA, balenine, carnosine, anserine and combinations thereof.

10. The composition of any previous clauses, wherein the composition is a drink.

11. The composition of any preceding clause, wherein the composition is a powder.

12. The composition of any preceding clause, wherein the supplement is in a solid oral dosage form.

13. The composition of any preceding clause, wherein the supplement is formulated for topical administration.

14. The composition of any preceding clause, except clause 9, wherein the composition is substantially free of caffeine.

15. A method for improving energy in subject, comprising: administering to the subject with the composition of clauses 1-14.

16. The method of clause 15, wherein upon administration of the composition, the subject experiences improvement of at least one of mood, energy, focus, concentration or sexual desire or a reduction of at least one of anxiety, fatigue, perception of effort or perception of pain.

17. The method of clause 16, wherein upon continued administration to the subject, the composition does not create dependence in the subject and/or withdrawal effect in the subject when continued use is ceased.

18. The method of clause 15, wherein the amount of cholinergic agent provided is from about 50 mg to about 400 mg.

19. The method of clause 15, wherein the subject experiences a decrease in fatigue of at least about 6 percent.

20. The method of clause 15, wherein the subject experiences an increase in energy of at least about 5 percent.

21. The method of clause 15, wherein the composition further comprises at least one ingredient selected from the group consisting of L-theanine, phosphatidylcholine, alpha-GPC (L-alpha glycerylphosphorylcholine), Citicoline (Cytidine diphosphate choline (CPD Choline)), Choline Bitartrate, Bacopa Monnieri, Phosphatidylserine, pilocarpine, and cevimeline *Amburana cearensis, Lippia sidoides, Paullinia cupana, Plathymiscium floribundum*, tetrahydrocurcumin, and *Solanum asperum* and/or combinations thereof, caffeine, theobromine, naringin, hesperidin, 2-(dimethylamino) ethanol (DMAE), DMAE bitartrate, magnolia bark, theanine, phosphatidylserine, ashwagandha, *Rhodiola*, taurine, tyrosine, n-acetyl-tyrsoine, macuna, sceletium *tortuosa*, 5-HTP, tryptophan, saffron, Vitamin D, SAMe, lions mane and huperzine A.

22. A method of increasing athletic endurance in a subject comprising administering to the subject the composition of any of clauses 15-21.

23. The method of clause 22, wherein the composition is the composition of any of clauses 5-13, and wherein the administration of paraxanthine and cholinergic agent produce a synergistic increase athletic endurance in the subject, relative to the administration of paraxanthine or cholinergic agent alone.

24. A method of treating a condition in a subject in need thereof, comprising administering to the subject the composition of any of clauses 15-21.

25. The method of clause 24, wherein the condition is selected from narcolepsy, epilepsy, attention deficit disorders, attention deficit hyperactivity syndrome (ADHD), cognitive deficit disorders, palsies, uncontrolled anger, migraine, substance abuse addictions, eating disorders, depression, anxiety disorders, traumatic head injury (TBI), concussion, Parkinson's disease, Alzheimer's, and dementia.

26. The method of clause 24, wherein the condition is a mood disorder.

27. The method of clause 26, wherein the mood disorder is depression.

28. The method of clause 27, wherein the subject has been diagnosed with depression or is at risk of depression.

29. The method of clause 24, wherein the condition is an anxiety disorder.

30. The method of clause 24, wherein the composition is administered in a therapeutically effective amount.

31. The method of clause 24, wherein the composition is administered in a prophylactically effective amount.

32. The method of clause 24, wherein the composition comprises cholinergic agent at an amount from about 2 mg to about 800 mg.

33. The method of clause 24, wherein the composition further comprises at least one ingredient selected from the group consisting of L-theanine, phosphatidylcholine, alpha-GPC (L-alpha glycerylphosphorylcholine), Citicoline (Cytidine diphosphate choline (CPD Choline)), Choline Bitartrate, Bacopa Monnieri, Phosphatidylserine, pilocarpine, and cevimeline *Amburana cearensis, Lippia sidoides, Paullinia cupana, Plathymiscium floribundum*, tetrahydrocurcumin, and *Solanum asperum* and/or combinations thereof, caffeine, theobromine, naringin, hesperidin, 2-(dimethylamino)) ethanol (DMAE), DMAE bitartrate, magnolia bark, theanine, phosphatidylserine, ashwagandha, *Rhodiola*, taurine, tyrosine, n-acetyl-tyrsoine, macuna, sceletium tortuosa, 5-HTP, tryptophan, saffron, Vitamin D, SAMe, lions mane and/or huperzine A.

34. A method of enhancing attention in a subject in need thereof comprising administering the composition of any of clauses 15-21.

35. A method of improving working memory in a subject in need thereof comprising administering a composition to the subject comprising the composition of any of clauses 15-21.

36. A method of improving cognitive performance in a subject comprising administering the composition of any of clause 15-21.

37. The method of clause 36, wherein improved cognitive function is measured by an increase in one or more of: attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behavior, speed of processing, reasoning, problem solving and/or social cognition.

38. The method of clause 36-37, wherein the subject has experience age-related cognitive decline. 39. The method clauses 36-37, wherein administration of the composition to the subject increases the level of BDNF in the subject.

40. A method for treating or preventing age-related cognitive decline in a subject in need thereof, comprising administering to the subject an effective amount of the composition of any of clauses 15-21.

41. The method of clause 40, wherein administration of the composition increases one or more of attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behavior, speed of processing, reasoning, problem solving and/or social cognition.

42. The method of clause 41, wherein administration of the composition to the subject increases levels of catalase and/or glutathione in the subject.

43. The method of clause 42, wherein the composition is the composition of any of clauses 15-21, and wherein the administration of paraxanthine and cholinergic agent produce a synergistic increase in catalase and/or glutathione in the subject, relative to the administration of paraxanthine or cholinergic agent alone.

44. The method of clause 41, wherein administration of the composition to the subject increases BDNF in the subject.

45. The method of clause 43, wherein the composition is the composition of any of clauses 9-13, and wherein the administration of paraxanthine and cholinergic agent produce a synergistic increase in BDNF in the subject, relative to the administration of paraxanthine or cholinergic agent alone.

46. The method of clause 41, wherein administration of the composition to the subject decreases the level of amyloid β-protein (AB) in the subject.

47. The method of clause 46, wherein administration of the composition is the composition of any of clauses 5-13, and wherein the administration of paraxanthine and cholinergic agent produce a synergistic decrease in AB in the subject, relative to the administration of paraxanthine or cholinergic agent alone.

48. A method for treating or preventing Alzheimer's disease in subject in need thereof, comprising administering to the subject an effective amount of the composition of any of clauses 1-13.

49. The method of clause 48, wherein administration of the composition is the composition of any of clauses 5-13, and wherein the administration of paraxanthine and cholinergic agent produce a synergistic decrease in Aβ in the subject, relative to the administration of paraxanthine or cholinergic agent alone.

50. The method of clause 48, wherein the subject has been diagnosed with Alzheimer's disease.

51. The method of clause 48, wherein the subject is at risk of Alzheimer's disease.

52. The method of clause 48, wherein the subject has been diagnosed with mild cognitive impairment.

53. A method for increasing muscle function in a subject, comprising:
administering to the subject the composition of any of clauses 1-13.

54. The method of clause 53, wherein the composition further comprises one or more compounds selected from the list consisting of: isoleucine, leucine, and valine, histidine, isoleucine, leucine, lysine, methionine, phenylalanine, threonine, tryptophan, valine, creatine, arginine, cysteine, glutamine, glycine, proline, tyrosine, carnitine, beta-alanine, taurine, and beta-hydroxy beta-methylbutyrate.

55. A composition for increasing energy in a subject comprising a cholinergic agent and/or theanine and paraxanthine.

56. The composition of clause 55, wherein the paraxanthine and cholinergic agent and/or theanine are each present in an amount from about 2 mg to about 800 mg.

57. The composition of clause 56, wherein the paraxanthine and cholinergic agent and/or theanine are each present in an amount from about amount from 50 mg to about 400 mg.

58. The composition of clause 57, further comprising an active agent, selected from a group consisting of: L-theanine, phosphatidylcholine, alpha-GPC (L-alpha glycerylphosphorylcholine), Citicoline (Cytidine diphosphate choline (CPD Choline)), Choline Bitartrate, Bacopa Monnieri, Phosphatidylserine, pilocarpine, and cevimeline *Amburana cearensis, Lippia sidoides, Paullinia cupana, Plathymiscium floribundum*, tetrahydrocurcumin, and *Solanum asperum* and/or combinations thereof, gallic acid, (+)-catechin (C), (–)-epicatechin (EC), (+)-gallocatechin (GC), (–)-epigallocatechin (EGC), (–)-catechin gallate (CG), (–)-gallocatechin gallate (GCG), (–)-epicatechin gallate (ECG) and (–)-epigallocatechin gallate (EGCG), glycerides, propylene glycol, lauroyl macrogol, lauroyl macrogol derivatives, co-crystallization products of bioperine, piperine, black pepper, bergamottin, dihydroxybergamottin (CYP3A4), flavonoids (naringin, hesperidin, nobiletin, tangeretin, quercetin), pterostilbene, fisetin, phytosomes, salicin, fish oil (omega-3 fatty acids and specialized, small lipid pro-resolving epoxide derivatives), oxylipins, tart cherry, krill oil, astaxanthin, proteolytic enzymes, glucosamine sulfate, chondroitin sulfate, MSM (methylsulfonylmethane), SAMe (S-adenosylmethionine), ASU (avocado-soybean unsapponifiable fraction), cetyl myristoleate, *Dolichos falcate*, triterpenoids, *Acacia catechu, Andrographis paniculata, Scutalleria baicalensis*, Agmatine sulfate, Stinging Nettle, Sea Buckthorn, Curcumin, Cissus Quadrilangularis, *Boswellia serrata, Wasabia japonica* (wasabi extract for Tea Tree Oil), Emu Oil, *Arnica, Mangifera indica* L. (Anacardiaceae), *Lagenaria breviflora, Zingiber officinale* (ginger & gingerols/shogaols), *Hoodia gordonii*, caffeine, yohimbine, methylsynephrine, synephrine, theobromine, tocopherols, theophylline, alpha-yohimbine, conjugated linoleic acid (CLA), octopamine, evodiamine, passion flower, red pepper, cayenne, raspberry ketone, guggul, green tea, guarana, kola nut, beta-Phenethylamines, *Acacia rigidula*, forskolin (*Coleus forskohlli*), theophylline, synephrine, yohimbine, *Rhodiola*, ashwagandha, *Ginseng, Ginkgo biloba*, siberian *Ginseng, astragalus*, licorice, green tea, reishi, dehydroepiandrosterone (DHEA), pregnenolone, tyrosine, N-acetyl-tyrosine, glucuronolactone, taurine, Acetyl-L-carnitine, 5-hydroxytryptophan, tryptophan, Phenethylamines, *Sceletium tortuosum* (and Mesembrine alkaloids), *Dendrobium* sp., *Acacia rigidula*, PQQ (Pyroloquinoline quinone), Ubiquinone(01), *Nicotinamide riboside*, picamilon, Huperzine A (Chinese clubmoss or *Huperzia serrata*, L-dopa, *Mucuna pruriens*, forskolin (*Coleus forskohlli*), 2-(dimethylamino) ethanol (DMAE), DMAE bitartrate, medium chain triglycerides, creatine, citrulline, arginine, lions mane, cordyceps, leucine, isoleucine, valine, BAIBA, ergothioneine, grains of paradise, Kanna, Huperzine A, ketones, Maca, *Ginseng*, ashwagandha, *Rhodiola*, theanine BCAAs, beta-alanine, fish oil, citrulline, arginine, hydroxy-methylbuterate, HICA, balenine, carnosine, anserine and combinations thereof.

59. The composition of clause 55, wherein administration of the composition to a subject produces a synergistic increase in energy relative to the administration of a comparable dose of paraxanthine or cholinergic agent alone.

60. The composition of clause 55, wherein cholinergic agent and paraxanthine are present at a ratio of about 4:1 to about 1:4.

61. A method for increasing energy in a subject comprising administering to the subject a composition comprising an effective amount of paraxanthine and of a cholinergic agent.

62. The method of clause 61, wherein the amount of cholinergic agent administered is from about 2 mg to about 800 mg.

63. The method of clause 61, wherein the subject experiences and increase in perception of energy of at least about 5%.

64. The method of clause 61, wherein the subject experiences a decrease of at least one of anxiety, fatigue, perception of effort, and/or perception of pain.

65. The method of clause 61, wherein the composition further comprises paraxanthine in an amount from about 2 mg to about 800 mg.

66. The method of clause 61, wherein the administration of paraxanthine and cholinergic agent produce a synergistic increase in perception of energy in the subject, relative to the administration of a comparable dose of paraxanthine or cholinergic agent alone.

67. The method of clause 61, wherein the composition further comprises at least one ingredient selected from the group consisting of Bitartrate, Bacopa Monnieri, Phosphatidylserine, pilocarpine, and cevimeline *Amburana cearensis, Lippia sidoides, Paullinia cupana, Plathymiscium floribundum*, tetrahydrocurcumin, and *Solanum asperum* and/or combinations thereof, caffeine, theobromine, naringin, hesperidin, 2-(dimethylamino) ethanol (DMAE), DMAE bitartrate, magnolia bark, theanine, phosphatidylserine, ashwagandha, *Rhodiola*, taurine, tyrosine, n-acetyl-tyrsoine, macuna, *Sceletium tortuosa*, 5-HTP, tryptophan, saffron, Vitamin D, SAMe, lions mane and huperzine A.

68. The method of clause 61, wherein the composition is substantially free of caffeine.

69. A method for improving athletic performance in a subject in comprising administering to the subject a composition comprising an effective amount of paraxanthine and a cholinergic agent.

70. The method of clause 69, wherein the amount of cholinergic agent administered is from about 50 mg to about 400 mg.

71. The method of clause 69, wherein athletic performance is increased by at least about 10%.

72. The method of clause 69, wherein the subject experiences and increase in endurance.

73. The method of clause 69, wherein the composition further comprises paraxanthine in an amount from about 2 mg to about 800 mg and wherein administration of the composition to a subject produces a synergistic increase in athletic performance to the administration of a comparable dose of paraxanthine or cholinergic agent alone.

74. A method for increasing energy in a subject comprising administering to the subject a composition comprising an effective amount of paraxanthine and of a theanine.

75. The method of clause 74, wherein the amount of theanine administered is from about 2 mg to about 800 mg.

76. The method of clause 74, wherein the subject experiences and increase in perception of energy of at least about 5%.

77. The method of clause 74, wherein the subject experiences a decrease of at least one of anxiety, fatigue, perception of effort, and/or perception of pain.

78. The method of clause 74, wherein the composition further comprises paraxanthine in an amount from about 2 mg to about 800 mg.

79. The method of clause 74, wherein the administration of paraxanthine and theanine produce a synergistic increase in perception of energy in the subject, relative to the administration of a comparable dose of paraxanthine or theanine alone.

80. The method of clause 74, wherein the composition further comprises at least one ingredient selected from the group consisting of Bitartrate, Bacopa Monnieri, Phosphatidylserine, pilocarpine, and cevimeline *Amburana cearensis, Lippia sidoides, Paullinia cupana, Plathymiscium floribundum*, tetrahydrocurcumin, and *Solanum asperum* and/or combinations thereof, caffeine, theobromine, naringin, hesperidin, 2-(dimethylamino) ethanol (DMAE), DMAE bitartrate, magnolia bark, theanine, phosphatidylserine, ashwagandha, *Rhodiola*, taurine, tyrosine, n-acetyl-tyrsoine, macuna, *Sceletium tortuosa*, 5-HTP, tryptophan, saffron, Vitamin D, SAMe, lions mane and huperzine A.

81. The method of clause 74, wherein the composition is substantially free of caffeine.

82. A method for improving athletic performance in a subject in comprising administering to the subject a composition comprising an effective amount of paraxanthine and a theanine.

83. The method of clause 82, wherein the amount of theanine administered is from about 50 mg to about 400 mg.

84. The method of clause 82, wherein athletic performance is increased by at least about 10%, 85. The method of clause 82, wherein the subject experiences and increase in endurance.

86. The method of clause 82, wherein the composition further comprises paraxanthine in an amount from about 2 mg to about 800 mg and wherein administration of the composition to a subject produces a synergistic increase in athletic performance to the administration of a comparable dose of paraxanthine or theanine alone.

EXAMPLES

The following examples are put forth so as to provide those of ordinary skill in the art with a complete disclosure and description of certain examples of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Example 1

Case Studies of Paraxanthine+Cholinergic Agent

To assess the effect of the combination of the paraxanthine (PX) and a cholinergic agent, seven subjects were administered PX (150 mg) as a pre-workout followed by a 6 day wash out. Subjects were then administered paraxanthine (between 150 and 300 mg) and alpha+GPC. Subjects reported that relative to the administration of PX alone, they experienced:

Increased exercise performance

Increased energy

Increased cognitive function

Increased sense of wellbeing/euphoria

Subjects further noted the lack of jittery and/or anxious feelings they had previously experienced with caffeine and reported no adverse effects on sleep.

Example 2

Energy, Endurance, Performance 1.1. Methods

Thirty-six 8-week-old male Swiss Albino mice were housed in an animal room at a constant temperature ($22\pm3°$ C.) and humidity (30%-70%) under a 12:12 h light-dark cycle with standard laboratory diet (Purina 5L79, Rat and Mouse 18% protein; PMI Nutrition International, Brentwood, MO, USA). Distilled water was provided ad libitum. All animal experiments were reviewed and approved by the Institutional Animal Ethical Committee (IAEC) of Radiant Research Services Pvt. Ltd (Bangalore, India). All research was conducted in accordance with the guidelines of the committee for the purpose of control and supervision of experiments on animals.

After one week of acclimation, the animals were randomly divided by body weight into six groups (n=6 per group in each test) for oral treatment once a day, at approximately same time each day (±1 hour), for 28 consecutive days: (1) vehicle control; (2) paraxanthine (3) Theobromine; (4) Theophylline (5) L-Alpha glycerylphosphorylcholine (alpha-GPC); and (6) paraxanthine plus alpha-GPC. The dose administered to the mice was calculated using US Food and Drug Administration for human equivalence doses (HED), assuming a human weight of 60 kg. The following HED were used in this study: 50 mg paraxanthine, (ENFINITY™, Ingenious Ingredients, L.P Lewisville, TX, USA; mouse dose: 10.275 mg/kg bw/day); 200 mg alpha-GPC mg (YangLing Daily Health Bio-Engineering Technology Co., Ltd., China; mouse dose: 41.09 mg/kg bw), 50 mg theobromine (mouse dose: 10.275 mg/kg bw), and 50 mg theophylline (mouse dose: 10.275 mg/kg bw), and 50 mg paraxanthine plus 200 mg alpha-GPC. 0.5% Carboxy Methyl Cellulose sodium was used as vehicle and the test item formulations were prepared daily. Dosing was conducted via oral gavage using disposable polypropylene syringes with sterilized stainless steel gavage tubes. The food intake and water consumption were monitored daily, and BW was recorded weekly. The last dose on day 28 was given 1 hour prior to testing.

1.2. Exercise Training

During the treatment period, exercise training was completed using a motorized treadmill (Exer 3/6, Columbus Instruments international, OH, USA) at a moderate intensity of 20 cm/sec as maximal running speed, an incline of ten degrees and a shock intensity of 0.2 mA, for ten minutes. The speed of the treadmill was manually adjusted by increasing the belt speed by 5 cm/sec every two minutes throughout the total duration of ten minutes. All animals were adapted to this procedure daily 60 minutes after dosing for five days in a week during the treatment period.

1.3. Treadmill Endurance Test

On 28th day of each respective treatment, all animals were subjected to a muscle endurance test. Muscle endurance was accomplished on a motorized treadmill at a low to moderate intensity of 5-50 cm/sec as maximal running speed, an incline of ten degrees and a shock intensity of 0.2 mA, with the belt speed being increased by 5 cm/sec every two minutes until it reaches 50 cm/sec. Animals were subjected to the treadmill test until exhaustion. Distance traveled (cm) was measured as a marker of exercise performance, energy, and endurance.

2. Results

The mice treated with paraxanthine showed significant improvements of exercise performance, energy, and endurance, compared to placebo, compared to alpha-GPC, and compared to the other caffeine metabolites (theobromine, theophylline). The combination of paraxanthine and alpha-GPC showed synergistic effects over paraxanthine or alpha-GPC alone.

Paraxanthine increased the distance travelled during treadmill exercise by 81% compared to control (placebo: 171.17±6.82 m, paraxanthine: 309.50±6.77 m), by 9.9% compared to theophylline (297.00±5.25 m), by 6.3% compared to theobromine (300.83±6.74 m), and by 4.4% over alpha-GPC (303.67±7.74 m). The combination of paraxanthine and alpha-GPC (317.83±6.37 m) showed 6.0% greater performance compared to paraxanthine, and 10.7% greater performance compared to alpha-GPC alone.

Example 3

Cognition, Memory, Learning, Age-Related Cognitive Decline, Mood 1.1. Methods

Thirty-six 8-week-old male Swiss Albino Wistar rats (young), and thirty-six 16-month-old male Swiss Albino Wistar rats (old) were housed in an animal room at a constant temperature (22±3° C.) and humidity (30%-70%) under a 12:12 h light-dark cycle with standard laboratory diet (Purina 5L79, Rat and Mouse 18% protein; PMI Nutrition International, Brentwood, MO, USA). Distilled water was provided ad libitum. All animal experiments were reviewed and approved by the Institutional Animal Ethical Committee (IAEC) of Radiant Research Services Pvt. Ltd (Bangalore, India). All research was conducted in accordance with the guidelines of the committee for the purpose of control and supervision of experiments on animals.

After one week of acclimation, the animals were randomly divided by body weight into six groups (n=6 in each test) for oral treatment once a day, at approximately same time each day (±1 hour), for 14 consecutive days: (1) vehicle control; (2) paraxanthine (3) Theobromine; (4) Theophylline (5) L-Alpha glycerylphosphorylcholine (alpha-GPC); and (6) paraxanthine plus alpha-GPC. The dose administered to the mice was calculated using US Food and Drug Administration for human equivalence doses (HED), assuming a human weight of 60 kg. The following HED were used in this study: 50 mg paraxanthine, (ENFINITY™, Ingenious Ingredients, L.P Lewisville, TX, USA; rat dose: 5.141 mg/kg bw/day); 200 mg alpha-GPC mg (YangLing Daily Health Bio-Engineering Technology Co., Ltd., China; rat dose: 20.566 mg/kg bw), 50 mg theobromine (rat dose: 5.141 mg/kg bw), and 50 mg theophylline (rat dose: 5.141 mg/kg bw), and 50 mg paraxanthine plus 200 mg alpha-GPC. 0.5% Carboxy Methyl Cellulose sodium was used as vehicle and the test item formulations were prepared daily. Dosing was conducted via oral gavage using disposable polypropylene syringes with sterilized stainless steel gavage tubes. The food intake and water consumption were monitored daily, and BW was recorded weekly. The last dose on day 14 was given 1 hour prior to testing.

1.2. Walter Morris Maze Test

The Walter Morris Maze test consisted of a circular pool in a room with geometric shapes on the wall serving as spatial cues. The pool, which is 70 cm in diameter and painted with black color, filled with 13 cm depth of 25±1° C. water. A platform (6 cm diameter) was placed into one quadrant of the pool and submerged 1 cm below the water surface. For the training, all rats were trained to locate the submerged platform in constant location. The training day consisted of four trials. During training, a rat started at one of four starting points and allowed to swim until it located the platform or until 60 seconds had elapsed. The rat was allowed to remain on the platform for 15 seconds before being dried off and later was transferred to a holding cage. If the rat did not reach the platform within 60 seconds, it was gently guided there by the experimenter. The animals were continuously trained 4 times at 4 starting points continued daily for 4 days, the main trial was conducted on the 15th & 16th day and the latency of escaping onto the platform was recorded.

2. Results 2.1. Young Animals 2.1.1 Cognitive Performance, Learning, Memory

Paraxanthine decreased the time the animals needed to reach the platform (escape latency) by 40% compared to control (placebo: 54.17±1.17 seconds, paraxanthine: 32.50±1.38 seconds), by 14.5% compared to theophylline (38.00±1.90 seconds), by 13.7% compared to theobromine (37.67±2.07 seconds), and by 6.7% over alpha-GPC (34.83±1.33 seconds). The combination of paraxanthine and alpha-GPC (27.33±1.97 seconds) showed 15.9% greater performance compared to paraxanthine, and 21.5% greater performance compared to alpha-GPC alone.

2.1.2 Neurotransmitter (Cognition, Mood), Neuroplasticity

Paraxanthine increased neuroplasticity (brain derived neuro factor, BDNF) compared to placebo by 22.7% (placebo: 747.23±5.20 μg/mL, paraxanthine: 917.05±5.21 pg/mL), by 4.9% compared to theophylline (874.15±8.72 μg/mL), by 5.4% compared to theobromine (870.00±9.98 μg/mL), and by 4.0% over alpha-GPC (881.70±10.41 μg/mL). The combination of paraxanthine and alpha-GPC (952.50±7.37 μg/mL) showed 3.9% greater increase in BDNF compared to paraxanthine, and 8.0% greater increase in BDNF compared to alpha-GPC alone.

Paraxanthine increased concentration of the neurotransmitters acetylcholine (Ach) and dopamine (dopa) compared to placebo by 23.9% (Ach: placebo: 53.94±1.82 U/mL, paraxanthine: 66.83±2.38 U/mL), and 23.7% (dopa: placebo: 469.15±5.39 ng/L, paraxanthine: 580.22±5.33 ng/L), respectively; by 4.6% and 6.7% respectively, compared to theophylline (Ach: 63.89±1.64 U/mL; dopa: 543.78±6.11 ng/L), by 4.0% and 5.0% compared to theobromine (Ach: 64.28±0.88 U/mL; dopa: 552.73±10.42 ng/L), and by 1.4% and 3.0% compared to alpha-GPC (Ach: 65.89±1.64 U/mL; dopa: 563.55±7.98 ng/L). The combination of paraxanthine and alpha-GPC (Ach: 71.94±2.15 U/mL; dopa: 589.78±3.94 ng/L) showed a 7.6% greater increase in Ach, and a 1.7% greater increase in dopa compared to paraxanthine, and 9.2% greater increase in Ach, and a 4.7% greater increase in dopa compared to alpha-GPC alone.

2.1.3 Antioxidant, Brain Protection

Paraxanthine increased levels of the antioxidant glutathione (GSH) compared to placebo by 64.1% (placebo: 19.85±0.68 μg/mL, paraxanthine: 32.57±0.84 μg/mL), by 9.4% compared to theophylline (29.78±1.07 μg/mL), by 3.9% compared to theobromine (31.28±0.78 μg/mL), and by 2.6% over alpha-GPC (31.72±0.53 μg/mL). The combination of paraxanthine and alpha-GPC (36.75±1.24 μg/mL) showed 12.8% greater increase in GSH compared to paraxanthine, and 15.8% greater increase in GSH compared to alpha-GPC alone.

2.2. Old Animals 2.2.1 Performance

Paraxanthine decreased the time the animals needed to reach the platform (escape latency) by 33.7% compared to control (placebo: 58.83±1.33 seconds, paraxanthine: 39.00±1.90 seconds), by 11.0% compared to theophylline (43.83±1.47 seconds), by 7.9% compared to theobromine (42.33±1.63 seconds), and by 2.1% over alpha-GPC (39.83±0.98 seconds). The combination of paraxanthine and alpha-GPC (35.83±1.94 seconds) showed 8.1% greater performance compared to paraxanthine, and 10.0% greater performance compared to alpha-GPC alone.

2.2.2 Neurotransmitter (Cognition, Mood), Neuroplasticity

Paraxanthine increased neuroplasticity (brain derived neuro factor, BDNF) compared to placebo by 18.1% (placebo: 713.72±4.11 μg/mL, paraxanthine: 842.68±6.26 pg/mL), by 3.8% compared to theophylline (811.83±4.56 μg/mL), by 3.1% compared to theobromine (817.72±6.26 μg/mL), and by 1.5% over alpha-GPC (881.70±10.41 μg/mL). The combination of paraxanthine and alpha-GPC (851.02±6.12 μg/mL) showed 1.0% greater increase in BDNF compared to paraxanthine, and 2.5% greater increase in BDNF compared to alpha-GPC alone.

Paraxanthine increased concentration of the neurotransmitters acetylcholine (Ach) and dopamine (dopa) compared to placebo by 23.2% (Ach: placebo: 48.50±1.41 U/mL, paraxanthine: 59.78±2.61 U/mL), and 32.7% (dopa: placebo: 389.38±8.85 ng/L, paraxanthine: 516.85±4.43 ng/L), respectively; by 8.0% and 4.2% respectively, compared to theophylline (Ach: 55.33±1.05 U/mL; dopa: 495.82±10.86 ng/L), by 5.5% and 2.8% compared to theobromine (Ach: 56.67±1.32 U/mL; dopa: 503.03±9.29 ng/L), and by 5.1% and 2.1% compared to alpha-GPC (Ach: 56.89±1.76 U/mL; dopa: 506.35±2.82 ng/L). The combination of paraxanthine and alpha-GPC (Ach: 61.50±0.69 U/mL; dopa: 534.87±3.67 ng/L)) showed a 2.9% greater increase in Ach, and a 3.5% greater increase in dopa compared to paraxanthine, and 8.1% greater increase in Ach, and a 5.6% greater increase in dopa compared to alpha-GPC alone.

2.2.3 Antioxidant, Brain Protection

Paraxanthine increased levels of the antioxidant glutathione (GSH) compared to placebo by 62.1% (placebo: 15.77±0.73 μg/mL, paraxanthine: 25.57±0.80 μg/mL), by 5.5% compared to theophylline (24.23±0.63 μg/mL), by 4.2% compared to theobromine (24.53±0.54 μg/mL), and by 3.4% over alpha-GPC (24.72±0.48 μg/mL). The combination of paraxanthine and alpha-GPC (27.37±0.75 μg/mL) showed 7.7% greater increase in GSH compared to paraxanthine, and 10.7% greater increase in GSH compared to alpha-GPC alone.

The combination of paraxanthine and alpha-GPC shows synergistic effect on increasing cognition performance and neurotransmitter levels in young and in old (age-related cognitive decline), mood (dopamine levels), neuroplasticity, and brain protection (antioxidant).

Example 4

Energy, Endurance, Performance 1.1. Methods

Twenty-four 8-week-old male Swiss Albino mice were housed in an animal room at a constant temperature (22±3° C.) and humidity (30%-70%) under a 12:12 h light-dark cycle with standard laboratory diet (Purina 5L79, Rat and Mouse 18% protein; PMI Nutrition International, Brentwood, MO, USA). Distilled water was provided ad libitum. All animal experiments were reviewed and approved by the Institutional Animal Ethical Committee (IAEC) of Radiant Research Services Pvt. Ltd (Bangalore, India). All research was conducted in accordance with the guidelines of the committee for the purpose of control and supervision of experiments on animals.

After one week of acclimation, the animals were randomly divided by body weight into four groups (n=6 per group in each test) for oral treatment once a day, at approximately same time each day (±1 hour), for 28 consecutive days: (1) vehicle control; (2) paraxanthine (3) L-Theanine; and (4) paraxanthine plus L-Theanine. The dose administered to the mice was calculated using US Food and Drug Administration for human equivalence doses (HED), assuming a human weight of 60 kg. The following HED were used in this study: 50 mg paraxanthine, (ENFINITY™ Ingenious Ingredients, L.P Lewisville, TX, USA; mouse dose: 10.275 mg/kg bw/day); 25 mg L-Theanine (mouse dose: 5.137 mg/kg bw), and 50 mg paraxanthine plus 25 mg L-Theanine. 0.5% Carboxy Methyl Cellulose sodium was used as vehicle and the test item formulations were prepared daily. Dosing was conducted via oral gavage using disposable polypropylene syringes with sterilized stainless steel gavage tubes. The food intake and water consumption were monitored daily, and BW was recorded weekly. The last dose on day 28 was given 1 hour prior to testing.

1.2. Exercise Training

During the treatment period, exercise training was completed using a motorized treadmill (Exer 3/6, Columbus Instruments international, OH, USA) at a moderate intensity of 20 cm/sec as maximal running speed, an incline of ten degrees and a shock intensity of 0.2 mA, for ten minutes. The speed of the treadmill was manually adjusted by increasing the belt speed by 5 cm/sec every two minutes throughout the total duration of ten minutes. All animals were adapted to this procedure daily 60 minutes after dosing for five days in a week during the treatment period. 1.3. Treadmill Endurance Test On 28th day of each respective treatment, all animals were subjected to a muscle endurance test. Muscle endurance was accomplished on a motorized treadmill at a low to moderate intensity of 5-50 cm/sec as maximal running speed, an incline of ten degrees and a shock intensity of 0.2 mA, with the belt speed being increased by 5 cm/sec every two minutes until it reaches 50 cm/sec. Animals were subjected to the treadmill test until exhaustion. Distance traveled (cm) was measured as a marker of exercise performance, energy and endurance.

2. Results

The mice treated with paraxanthine showed significant improvements of exercise performance, energy, and endurance, compared to placebo and compared to L-Theanine. The combination of paraxanthine and L-Theanine showed synergistic effects over paraxanthine or L-Theanine alone.

Paraxanthine increased the distance travelled during treadmill exercise by 81% compared to control (placebo: 171.17±6.82 m, paraxanthine: 309.50±6.77 m), and by 4.9% over L-Theanine (295.17±6.11 m). The combination of paraxanthine and L-Theanine (313.50±6.28 m) showed 1.3% greater performance compared to paraxanthine, and 6.2% greater performance compared to L-Theanine alone.

Example 4

Cognition, Memory, Learning, Age-Related Cognitive Decline 1.1. Methods

Twenty-four 8-week-old male Swiss Albino Wistar rats (young), and Twenty-four 16-month-old male Swiss Albino Wistar rats (old) were housed in an animal room at a constant temperature (22±3° C.) and humidity (30%-70%) under a 12:12 h light-dark cycle with standard laboratory diet (Purina 5L79, Rat and Mouse 18% protein; PMI Nutrition International, Brentwood, MO, USA). Distilled water was provided ad libitum. All animal experiments were reviewed and approved by the Institutional Animal Ethical Committee (IAEC) of Radiant Research Services Pvt. Ltd (Bangalore, India). All research was conducted in accordance with the guidelines of the committee for the purpose of control and supervision of experiments on animals.

After one week of acclimation, the animals were randomly divided by body weight into six groups (n=6 in each test) for oral treatment once a day, at approximately same time each day (±1 hour), for 14 consecutive days: (1) vehicle control; (2) paraxanthine (3) L-Theanine; and (4) paraxanthine plus L-Theanine. The dose administered to the mice was calculated using US Food and Drug Administration for human equivalence doses (HED), assuming a human weight of 60 kg. The following HED were used in this study: 50 mg paraxanthine, (ENFINITY™, Ingenious Ingredients, L.P Lewisville, TX, USA; rat dose: 5.141 mg/kg bw/day); 25 mg L-Theanine (rat dose: 2.570 mg/kg bw), and 50 mg paraxanthine plus 25 mg L-Theanine. 0.5% Carboxy Methyl Cellulose sodium was used as vehicle and the test item formulations were prepared daily. Dosing was conducted via oral gavage using disposable polypropylene syringes with sterilized stainless steel gavage tubes. The food intake and water consumption were monitored daily, and BW was recorded weekly. The last dose on day 14 was given 1 hour prior to testing.

1.2. Walter Morris Maze Test

The Walter Morris Maze test consisted of a circular pool in a room with geometric shapes on the wall serving as spatial cues. The pool, which is 70 cm in diameter and painted with black color, filled with 13 cm depth of 25±1°

C. water. A platform (6 cm diameter) was placed into one quadrant of the pool and submerged 1 cm below the water surface. For the training, all rats were trained to locate the submerged platform in a constant location. The training day consisted of four trials. During training, a rat started at one of four starting points and allowed to swim until it located the platform or until 60 seconds had elapsed. The rat was allowed to remain on the platform for 15 seconds before being dried off and later was transferred to a holding cage. If the rat did not reach the platform within 60 seconds, it was gently guided there by the experimenter. The animals were continuously trained 4 times at 4 starting points continued daily for 4 days, the main trial was conducted on the 15th & 16th day and the latency of escaping onto the platform was recorded.

2. Results 2.1. Young Animals 2.1.1 Cognitive Performance, Learning, Memory

Paraxanthine decreased the time the animals needed to reach the platform (escape latency) by 40% compared to control (placebo: 54.17±1.17 seconds, paraxanthine: 32.50±1.38 seconds), and by 15.2% over L-Theanine (38.33±2.07 seconds). The combination of paraxanthine and L-Theanine (29.67±1.63 seconds) showed 9.5% greater performance compared to paraxanthine, and 22.6% greater performance compared to L-Theanine alone.

2.1.2 Neurotransmitter (Cognition, Mood), Neuroplasticity

Paraxanthine increased neuroplasticity (brain derived neuro factor, BDNF) compared to placebo by 22.7% (placebo: 747.23±5.20 μg/mL, paraxanthine: 917.05±5.21 μg/mL), and by 5.9% over L-Theanine (865.85±8.66 μg/mL). The combination of paraxanthine and L-Theanine (928.48±9.97 μg/mL) showed 1.3% greater increase in BDNF compared to paraxanthine, and 7.2% greater increase in BDNF compared to L-Theanine alone.

Paraxanthine increased concentration of the neurotransmitters acetylcholine (Ach) and dopamine (dopa) compared to placebo by 23.9% (Ach: placebo: 53.94±1.82 U/mL, paraxanthine: 66.83±2.38 U/mL), and 23.7% (dopa: placebo: 469.15±5.39 ng/L, paraxanthine: 580.22±5.33 ng/L), respectively; and by 6.4% and 9.8% compared to L-Theanine (Ach: 62.83±0.91 U/mL; dopa: 528.18±4.09 ng/L). The combination of paraxanthine and L-Theanine (Ach: 70.94±1.57 U/mL; dopa: 587.90±4.91 ng/L) showed a 6.2% greater increase in Ach, and a 1.3% greater increase in dopa compared to paraxanthine, and 12.9% greater increase in Ach, and a 11.3% greater increase in dopa compared to L-Theanine alone.

2.1.3 Antioxidant, Brain Protection

Paraxanthine increased levels of the antioxidant glutathione (GSH) compared to placebo by 64.1% (placebo: 19.85±0.68 μg/mL, paraxanthine: 32.57±0.84 μg/mL), and by 2.6% over L-Theanine (31.72±0.53 μg/mL). The combination of paraxanthine and L-Theanine (36.75±1.24 μg/mL) showed 12.8% greater increase in GSH compared to paraxanthine, and 15.8% greater increase in GSH compared to L-Theanine alone.

2.2. Old Animals 2.2.1 Cognitive Performance, Learning, Memory

Paraxanthine decreased the time the animals needed to reach the platform (escape latency) by 33.7% compared to control (placebo: 58.83±1.33 seconds, paraxanthine: 39.00±1.90 seconds), and by 12.7% over L-Theanine (44.67±2.16 seconds). The combination of paraxanthine and L-Theanine (36.17±1.72 seconds) showed 7.3% greater performance compared to paraxanthine, and 19.0% greater performance compared to L-Theanine alone.

2.2.2 Neurotransmitter (Cognition, Mood), Neuroplasticity

Paraxanthine increased neuroplasticity (brain derived neuro factor, BDNF) compared to placebo by 18.1% (placebo: 713.72±4.11 μg/mL, paraxanthine: 842.68±6.26 μg/mL), and by 6.8% over L-Theanine (789.07±2.03 μg/mL). The combination of paraxanthine and L-Theanine (846.27±6.19 μg/mL) showed 0.4% greater increase in BDNF compared to paraxanthine, and 7.3% greater increase in BDNF compared to L-Theanine alone.

Paraxanthine increased concentration of the neurotransmitters acetylcholine (Ach) and dopamine (dopa) compared to placebo by 23.3% (Ach: placebo: 48.50±1.41 U/mL, paraxanthine: 59.78±2.61 U/mL), and 32.7% (dopa: placebo: 389.38±8.85 ng/L, paraxanthine: 516.85±4.43 ng/L), respectively; and by 7.0% and 9.3% compared to L-Theanine (Ach: 55.89±1.05 U/mL; dopa: 473.03±6.05 ng/L). The combination of paraxanthine and L-Theanine (Ach: 61.44±1.24 U/mL; dopa: 527.02±4.75 ng/L) showed a 2.8% greater increase in Ach, and a 2.0% greater increase in dopa compared to paraxanthine, and 9.9% greater increase in Ach, and a 11.4% greater increase in dopa compared to L-Theanine alone.

2.2.3 Antioxidant, Brain Protection

Paraxanthine increased levels of the antioxidant glutathione (GSH) compared to placebo by 62.1% (placebo: 15.77±0.73 μg/mL, paraxanthine: 25.57±0.80 μg/mL), and by 7.1% over L-Theanine (23.87±0.45 μg/mL). The combination of paraxanthine and L-Theanine (26.75±0.38 μg/mL) showed 4.6% greater increase in GSH compared to paraxanthine, and 12.1% greater increase in GSH compared to L-Theanine alone.

The combination of paraxanthine and alpha-GPC shows synergistic effect on increasing cognition performance and neurotransmitter levels in young and in old (age-related cognitive decline), mood (dopamine levels), neuroplasticity, and brain protection (antioxidant).

Although the disclosure has been described with reference to preferred embodiments, persons skilled in the art will recognize that changes may be made in form and detail without departing from the spirit and scope of the disclosed apparatus, systems and methods.

What is claimed is:

1. A method for improving physical performance in a subject, comprising: providing the subject with a composition comprising about 50 mg to about 800 mg of paraxanthine and an effective amount of alpha-GPC (L-alpha glycerylphosphorylcholine).

2. The method of claim 1, wherein paraxanthine is present in the composition in an amount from about 50 mg to about 400 mg.

3. The method of claim 2, wherein the alpha-GPC is present in the composition in an amount from about 50 mg to about 400 mg.

4. The method of claim 2, wherein the composition is substantially free of caffeine.

5. The method of claim 2, wherein administration of the composition to a subject produces a synergistic increase in physical performance relative to the administration of a comparable dose of paraxanthine or alpha-GPC.

6. The method of claim 1 further comprising a paraxanthine congener or paraxanthine analog selected from the group consisting of caffeine, methyl caffeine, theobromine, theophylline, liberine, methylliberine, theacrine and combinations thereof.

7. The method of claim 6, wherein the paraxanthine congener or paraxanthine analog is caffeine.

8. A method of improving cognitive function in a subject comprising administering to the subject a composition comprising about 50 mg to about 800 mg of paraxanthine and an effective amount of alpha-GPC.

9. The method of claim 8, wherein administration of the composition increases one or more of attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behavior, speed of processing, reasoning, problem solving and/or social cognition.

10. The method of claim 9, wherein administration of the composition enhances dopaminergic tone, cholinergic tone, and/or brain BDNF levels.

11. The method of claim 8, wherein administration of the composition is neuroprotective against oxidative stress.

12. The method of claim 8 further comprising a paraxanthine congener or paraxanthine analog selected from the group consisting of caffeine, methyl caffeine, theobromine, theophylline, liberine, methylliberine, theacrine and combinations thereof.

13. The method of claim 8, wherein the alpha-GPC is present in the composition in an amount from about 50 mg to about 400 mg.

14. The method of claim 8, wherein the composition is substantially free of caffeine.

15. The method of claim 8, wherein administration of the composition to a subject produces a synergistic increase in cognitive function relative to the administration of a comparable dose of paraxanthine or alpha-GPC.

16. A method for enhancing energy in a subject comprising administering to the subject a composition comprising about 50 mg to about 800 mg of paraxanthine and an effective amount of alpha-GPC.

* * * * *